(12) United States Patent
Tse

(10) Patent No.: US 7,146,987 B2
(45) Date of Patent: Dec. 12, 2006

(54) ASSEMBLY FOR FLOSSING TEETH

(76) Inventor: James Tse, 12 Larkfield Drive, Toronto, ONT (CA) M3B 2H1

( * ) Notice: Subject to any disclaimer, the term of this patent is extended or adjusted under 35 U.S.C. 154(b) by 221 days.

(21) Appl. No.: 10/886,540

(22) Filed: Jul. 9, 2004

(65) Prior Publication Data

US 2006/0005855 A1    Jan. 12, 2006

(51) Int. Cl.
*A61C 15/00* (2006.01)
(52) U.S. Cl. .................................... 132/323
(58) Field of Classification Search ............ 132/321, 132/323; 206/663.5, 63.3, 388, 368; D28/65, D28/66, 67, 68
See application file for complete search history.

(56) References Cited

U.S. PATENT DOCUMENTS

| | | | | |
|---|---|---|---|---|
| 3,696,821 A * | 10/1972 | Adams, IV | ................ | 132/324 |
| 3,802,445 A * | 4/1974 | Wesley | ................ | 132/321 |
| 3,901,251 A * | 8/1975 | Johnston | ................ | 132/325 |
| 4,034,770 A * | 7/1977 | Trecker | ................ | 132/321 |
| 4,162,687 A * | 7/1979 | Lorch | ................ | 132/323 |
| 4,403,625 A * | 9/1983 | Sanders et al. | ................ | 132/323 |
| 4,519,408 A * | 5/1985 | Charatan | ................ | 132/321 |
| 4,638,824 A * | 1/1987 | De La Hoz | ................ | 132/323 |
| 4,986,289 A * | 1/1991 | McWhorter | ................ | 132/323 |
| 5,322,077 A * | 6/1994 | Corella | ................ | 132/323 |
| 5,454,386 A * | 10/1995 | Dix | ................ | 132/323 |
| 5,653,246 A * | 8/1997 | Wei et al. | ................ | 132/323 |

* cited by examiner

*Primary Examiner*—Todd E. Manahan

(57) ABSTRACT

A dental floss assembly including a dental floss with terminal ends; a hermetically sealed compartment for containing the dental floss; a first loop and a second loop, each loop attached to a different terminal end of the dental floss, and each loop outlining an open region; wherein at least one loop is separably attached to the compartment.

15 Claims, 3 Drawing Sheets

ASSEMBLY FOR FLOSSING TEETH

FIELD OF THE INVENTION

The invention relates to a dental floss assembly. More particularly, it relates to such an assembly with a floss compartment.

BACKGROUND OF THE INVENTION

Dental floss has been recommended by dental professionals as a necessity for maintaining optimal dental hygiene. If properly used, it can prevent the onset of gum disease such as gingivitis or cavity in those flossed areas.

Typically, a dental floss has a floss, which when in use is stretched at least in a partial section in a taut state so as to allow a scraping motion of the tautly stretched portion across a surface of a tooth. The scraping motion loosens debris on the dental surface, usually removing the debris from the flossed section and leaving the surface in a cleaner state. The removal of the debris results in better hygiene.

However, its acceptance by the general public has been limited, even after decades of warnings from dental associations. People find proper flossing tedious, uncomfortable and difficult. To reach and adequately floss all the necessary places with the floss requires time, manual dexterity and discipline. Electromechanical devices, developed thus far to make flossing an easier and more conducive task, have been shown by research to be inferior than conventional manual flossing, further to the relative disadvantage of significantly high cost.

As shown by the art in this field, many attempts have been made to make flossing more acceptable.

SUMMARY OF THE INVENTION

In a first aspect the invention provides a dental floss assembly comprising a dental floss having terminal ends; a hermetically sealed compartment for containing the dental floss; a first loop and a second loop, each loop attached to a different terminal end of the dental floss, and each loop outlining an open region; wherein at least one loop is separably attached to the compartment.

In one variation, the loops are approximately the same size and shape. Each open region is of approximately 1.5 centimeter diameter.

The loops are positioned in the same plane when attached to the compartment.

The loops may be positioned in parallel planes when attached to the compartment. With sides of the compartment being flush with edges of the loops.

In a preferred embodiment, the cross section of the first loop is C-shaped defining a first cavity; and the second loop is removably received in the first cavity.

In a variation of the above, the cross-section of the second loop is C-shaped defining a second cavity; the dental floss is wound around the second loop in the second cavity; and the compartment is formed as a combination of the second loop received in the first cavity.

In a further variation, the second cavity opens in a direction perpendicular to a plane defined by the open region of the second loop. Alternatively, the second cavity may open in a direction parallel to a plane defined by the open region of the second loop.

The invention also includes the assembly with a window defined by the first loop; a flange formed on the second loop for extending through and past the window when the second loop is received in the first cavity.

A tab may be attached to each of the first and second loops for separating the first loop from the second loop.

In the preferred embodiment, the compartment may be attached only to the first loop, or attached to the first loop and the second loop.

The loops may be made of plastic in construction.

The shape of the loops may be circular, triangular, square, rectangular, or hook-like.

BRIEF DESCRIPTION OF THE DRAWINGS

For a better understanding of the present invention and to show more clearly how it may be carried into effect, reference will now be made, by way of example, to the accompanying drawings which show preferred embodiments of the present invention and in which.

DETAILED DESCRIPTION OF THE PREFERRED EMBODIMENTS

Figure 2:
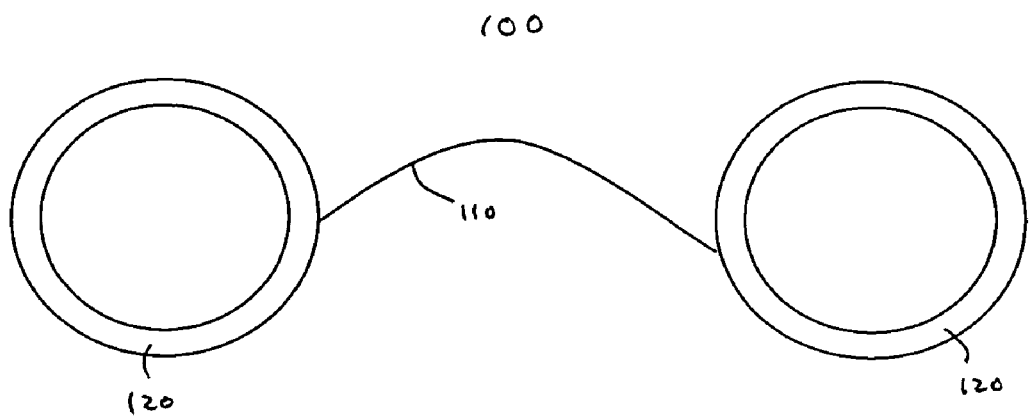
FIG. 2 is a top view of the assembly of FIG. 1 in the packaged state.

Referring to FIG. 2 showing a preferred embodiment of the dental floss assembly 100 in unpackaged state (usable for flossing). The assembly 100 has a floss 110 with the ends of the floss attached to separate finger grips 120. In this document, these finger grips 120 will be denoted as loops 120 even if the shape of the grips 120 are not necessarily (but are preferably) circular in shape. The finger grips 120 may also be hook-like in shape, that is to say, an unclosed circular loop. The loops 120 may also be roughly triangular or even rectangular. The purpose of the loops 120 is to accommodate fingers (preferably index) of a user while flossing teeth for stretching the floss 110 taut; as such the open regions defined by the loops 120 should be not much larger in diameter than a typical index finger (about 1.5 cm). Variations may be to accommodate smaller digits of a child.

Figure 1:
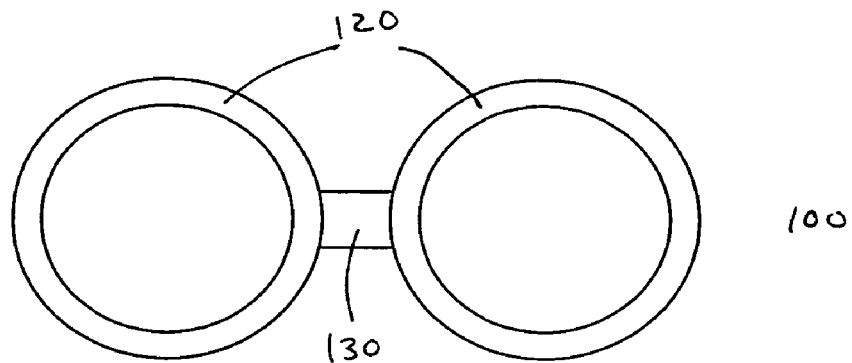
FIG. 1 is a top view of a dental floss assembly in the unpackaged state according to a preferred embodiment of the present invention.

The dental floss assembly 100 may also be in a stored state, as shown in FIG. 1 as the preferred embodiment of FIG. 1. The two loops 120 are joined side-by-side by a compartment 130 which houses the floss 110 (not shown). The compartment 130 is of sufficient size to house the floss 110 and may be constructed of any material and configuration which allows the loops 120 to be manually pulled apart from each other (or from the compartment 130), releasing the floss 110 and putting the assembly 100 into its unpackaged state. A preferred material is plastic; however any other light weight material resistant to breaking may be used.

A characteristic of the compartment 130 is that a hermetically sealed environment is provided thereby for ensuring that the floss 110 housed therein remains in a hygienic state when the floss assembly 100 is in the stored state until the compartment 130 is breached in order to use the assembly 100 for flossing. For example, a sealant may be applied to a plastic casing (not shown) for the floss 110. The plastic casing may be partially perforated to facilitate breaking apart.

Embodiments of the invention include a compartment 130 which joins the loops 120 of an assembly 100 in the stored state as in FIG. 1.

In a variation of the above (not shown), the loops 120 are placed in parallel planes with the compartment 130 interconnecting the loops 120. The sides of the compartment 130 may be flush with the edges of the loops 120 such that a top view of the assembly 100 shows a single circular ring. Alternatively, the compartment 130 may sit, similar to a jewel, on astride both loops 120.

Figure 3:
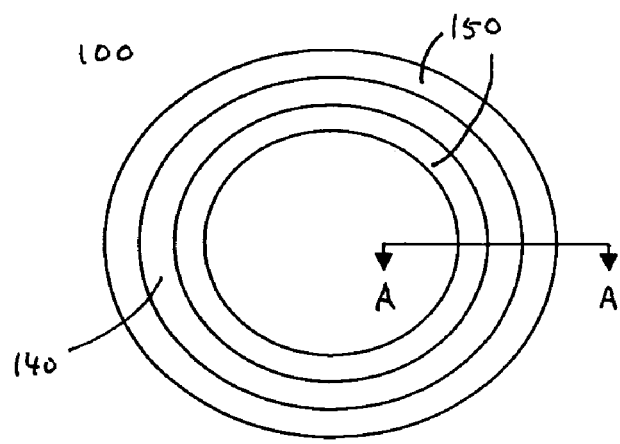
FIG. 3 is a top view of a dental floss assembly in the unpackaged state according to further embodiments of the present invention.
Figure 4A:
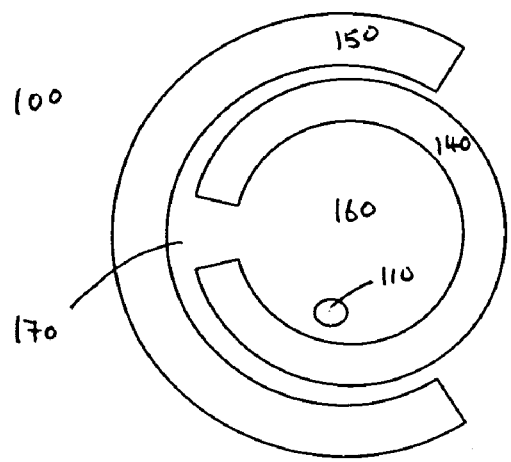
FIG. 4A is an exploded side cross-sectional view along the line A-A' of FIG. 3 for one embodiment.

Additional embodiments of the assembly 100 have loops 120 of different dimensions (FIG. 3): a major loop 150 of a larger diameter and a minor loop of a smaller dimension 140. In one variation, the major loop 150 has a C-shaped cross-sectional area defining a major cavity 170 (as shown in FIG. 4A). The major cavity 170 opens in a direction perpendicular to the plane defined by the opening region of the major loop 150. The minor loop 140 is dimensioned to fit inside the cavity 170 defined by the cross-section of the major loop 150 and can be inserted or removed from within the cavity manually, when the assembly 100 is in the stored or packaged state. In such a configuration, either or both the loops 140 150 may be made of a resilient material to permit extrication of one loop 120 from the other loop 120.

Figure 4B:
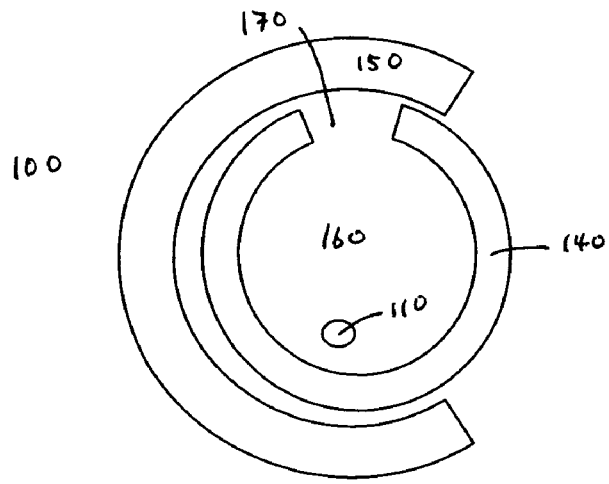
FIG. 4B is an exploded side cross-sectional view along the line A-A' of FIG. 3 for a second embodiment.

The minor loop 140 may also be C-shaped in cross-section (the minor cavity 160), with its cavity 160 housing the floss 110 (shown as wound once around the minor loop 140 in FIG. 4A, configurations of more are within invention, esp. if the major cavity 170 is used to keep used portions of the floss 110 during flossing), which may be wound a number of times around the minor loop 140 in the minor cavity 160. In the stored state, the minor cavity 160 may open to any side of the enclosing major loop 150. In FIG. 4B, the minor cavity 160 opens in a direction transverse to the plane defined by the minor loops 120. The combination of the sides of the loops 120 defines the compartment 130 and provides a good seal for keeping the floss 110 hygienic for later flossing when the assembly 100 is in the stored state.

Figure 4C:
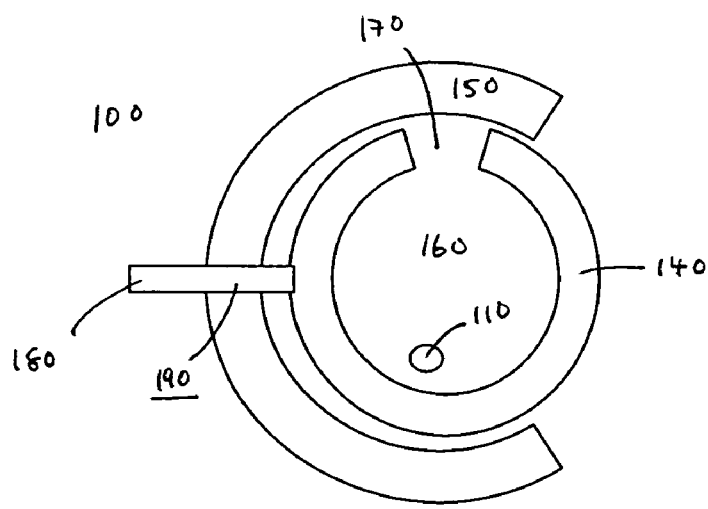
FIG. 4C is an exploded side cross-sectional view along the line A-A' of FIG. 3 for one embodiment showing flange and window.

One possible way for changing the assembly 100 in this latter configuration from the packaged to the unpackaged state is to provide for a flange 180 on the minor loop 140 extending in the same plane as that defined by the minor loop 140 (see FIG. 4C); the major loop 150 defines a window 190 through which the flange 180 may extend when the assembly 100 is in the unpackaged state. To unpackage the assembly 100, a user would apply pressure to the flange 180 while keeping the major loop 150 relatively immobile. One method by which this can be achieved is to put the assembly 100 against a hard surface with the flange 180 abutting the surface. Pressing the assembly 100 against the surface, such as by way of using one's palm, would push the flange 180 back out the window 190 at least partially, and remove the minor loop 140 from the major cavity 170 and allow the assembly 100 to be used for flossing.

The two loops 140 150 may also be separated by various other ways. For example, a tab (not shown) in the form of a rigid extension may be attached to, or form part of, each of the loops 140 150 (a string may also be sufficient). By pulling on the tab, the loops 140 150 may be parted from each other.

Figure 5:
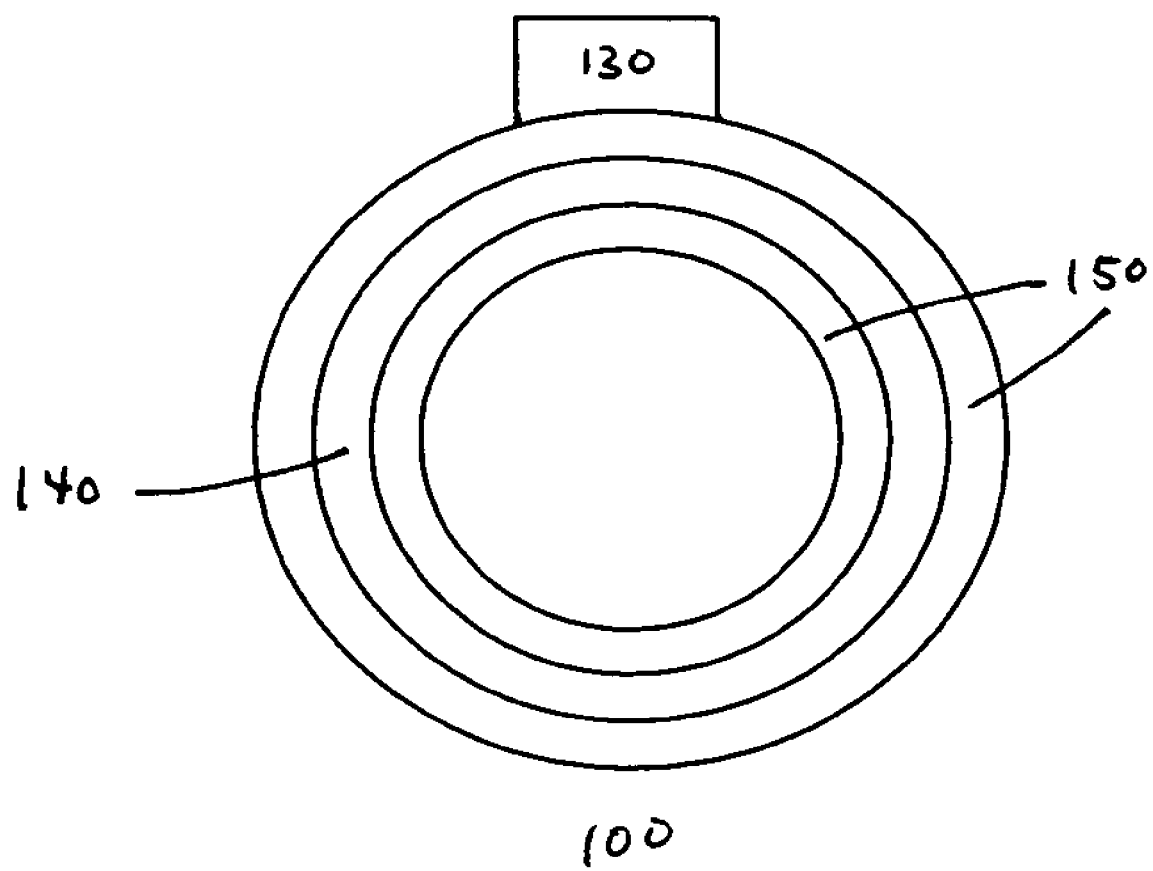
FIG. 5 is a top view of a dental floss assembly in the unpackaged state according to another embodiment of the present invention.

In a variation of the above (FIG. 5), the compartment 130 is not defined by the sides of the loops 120; rather, the compartment 130 is separate and positioned on the major loop 150 extending away from the major loop 150. This assembly 100 resembles a ring (jewellery), and may be conducive to use by children.

In variations, the separate compartment 130 resides between the major loop 150 and minor loop 140 (not shown), or the compartment 130 may partially overlap the minor loop 140 (not shown). In these configurations, the dimensions of the loops 120 are not so different as to cause a problem for flossing using the assembly 100.

The above description contains reference to dimensions. These are typical only and the invention is not limited to them. For example, a particular assembly may refer to dimension, however alternate embodiments could be configured with consequent modification to the dimensions, other quantities and materials to match the need of the person using the dental floss assembly.

It will be appreciated that the above description relates to the preferred embodiments by way of example only. Many variations on the apparatus for delivering the invention will be clear to those knowledgeable in the field, and such variations are within the scope of the invention as described and claimed, whether or not expressly described.

What is claimed is:

1. A dental floss assembly comprising:
   a dental floss having terminal ends;
   a hermetically sealed compartment for containing the dental floss;
   a first loop and a second loop, each loop attached to a different terminal end of the dental floss, and each loop outlining an open region
   wherein:
   at least one loop is separably attached to the compartment;
   the cross section of the first loop is C-shaped defining a first cavity; and
   the second loop is removably received in the first cavity.

2. The dental floss assembly of claim 1, wherein the loops are approximately the same size and shape.

3. The dental floss assembly of claim 2, wherein the loops are positioned in the same plane when attached to the compartment.

4. The dental floss assembly of claim 2, wherein the loops are positioned in parallel planes when attached to the compartment.

5. The dental floss assembly of claim 4, wherein sides of the compartment are flush with edges of the loops.

6. The dental floss assembly of claim 1, wherein each open region is of approximately 1.5 centimeter diameter.

7. The dental floss assembly of claim 1, wherein:
   the cross-section of the second loop is C-shaped defining a second cavity;
   the dental floss is wound around the second loop in the second cavity; and
   the compartment is formed as a combination of the second loop received in the first cavity.

8. The dental floss assembly of claim 7, wherein the second cavity opens in a direction perpendicular to a plane defined by the open region of the second loop.

9. The dental floss assembly of claim 7, wherein the second cavity opens in a direction parallel to a plane defined by the open region of the second loop.

10. The dental floss assembly of claim 1, further comprising:
   a window defined by the first loop;
   a flange formed on the second loop for extending through and past the window when the second loop is received in the first cavity.

11. The dental floss assembly of claim 1, further comprising a tab attached to each of the first and second loops for separating the first loop from the second loop.

12. The dental floss assembly of claim 1, wherein the compartment is attached to either only the first loop or both the first loop or the second loop.

13. The dental floss assembly of claim 1, wherein the compartment comprises a plastic casing and a sealant applied to the casing.

14. The dental floss assembly of claim 1, wherein the loops and compartment are made of plastic.

15. The dental floss assembly of claim 1, wherein the shape of the loops is chosen from the group of shapes consisting of circle, triangle, square, rectangle, and hook.

* * * * *